United States Patent [19]

Tonariya et al.

[11] Patent Number: 5,160,724
[45] Date of Patent: Nov. 3, 1992

[54] BARIUM SULFATE CONTRAST MEDIUM FOR X-RAY EXAMINATION OF THE LARGE INTESTINE

[75] Inventors: Yoshito Tonariya, Tokyo; Yukihito Wada, Saitama; Kazuhiro Yamaguchi, Higashimatsuyama; Tomio Yamazaki, Saitama; Isamu Sakai, Funabashi; Shigeru Yokoi, Tokyo; Mitsuo Togashi, Oyama; Yukihiro Noguchi, Omiya, all of Japan

[73] Assignee: Ohta Seiyaku Kabushiki Kaisha, Saitama, Japan

[21] Appl. No.: 409,296

[22] Filed: Sep. 19, 1989

[30] Foreign Application Priority Data

Sep. 22, 1988 [JP] Japan .................. 63-236272

[51] Int. Cl.$^5$ .......................... A61K 49/4; A61K 33/14
[52] U.S. Cl. ........................................ 424/4; 424/677; 514/966; 514/975
[58] Field of Search ................ 424/4, 677; 514/966, 514/975

[56] References Cited

U.S. PATENT DOCUMENTS

| 3,689,630 | 9/1972 | Kikuchi et al. | 424/4 |
| 4,069,306 | 1/1978 | Rothman | 424/4 |
| 4,120,946 | 10/1978 | Queville | 424/4 |

FOREIGN PATENT DOCUMENTS

| 108618 | 3/1934 | Hungary . |
| 55-127327 | 10/1980 | Japan . |
| 60-69041 | 4/1985 | Japan . |
| 8404888 | 12/1984 | World Int. Prop. O. . |

OTHER PUBLICATIONS

Wang, H. et al. Yaoxue Xuebao 16(8):610–617 (1981) [From Chem. Abs. 96:577326 (1982)].
F Pawlaczyk et al Acta Pol. Pharm. 31(3):367–72 (1974) [From Chem. Abs. 82:77063y (1975)].
Gafttanu, Eliza et al. Chem. Abstracts CA 103(10):76231s (1984).
Okahashi, Susumu Chem. Abstracts CA 103(6):42477m (1985).
Medline Abstract No. 85049978 (1984).
Medline Abstract No. 85105653 (1985),

*Primary Examiner*—Richard L. Raymond
*Assistant Examiner*—Gary E. Hollinden
*Attorney, Agent, or Firm*—Birch, Stewart, Kolasch & Birch

[57] ABSTRACT

A new barium sulfate contrast medium comprising 20 to 30 w/v % barium sulfate, gum tragacanth and either sodium carboxymethyl cellulose or gum arabic is useful for x-ray examination of the large intestine having adequate radiolucency combined with high coating abilities.

1 Claim, 6 Drawing Sheets

BARIUM SULFATE CONTRAST MEDIUM FOR X-RAY EXAMINATION OF THE LARGE INTESTINE

DETAILED DESCRIPTION OF THE INVENTION

1. Technical Field

This invention relates to a barium sulfate contrast medium for enema with double contrast method and computed tomography (X-ray CT) in X-ray examination of the large intestine (colon) practiced in the medical field.

2. Background Art

In recent years, with the change in food life to European and American styles in Japan, large intestine cancer is remarkably increasing and importance of large intestine examination method has been rapidly recognized Nowadays, progress and propagation of diagnostic imaging by computed tomography (X-ray CT), ultrasonication examination (US) and further magnetic resonance examination (MRI) are remarkable, and have been also incorporated into the diagnostic region of tubular organs such as the large intestine. However, most of large intestine diseases are lesions occurring in mucosa, and for discovery of such lesions, as a matter of course, but also for grasping of characteristics of the lesions, endoscopy and enema X-ray examination have been utilized as the main current.

The enema X-ray examination methods known in the prior art may be broadly classified into the filling method, the double contrast method, the compression method, the mucosal relief method, etc., and according to the present standard of Ministry of Health and Welfare of Japan (reevaluation result), it is approved to use 200 to 2000 ml of a 20 to 130 W/V % barium sulfate contrast medium. Among them, since the barium enema with double contrast method is optimum for imaging of lesions and diagnosis thereof, it holds the primary place in the current examinations.

The barium enema with double contrast method is a method, in which barium sulfate which is a positive contrast medium, is coated as a thin layer on the inner walls of the large intestine, and air which is a negative contrast medium is simultaneously insufflated to inflate the large intestine, whereby the state of the large intestine mucosa surface is imaged with contrast on a X-ray film.

The enema with double contrast method includes the Fisher method (1923) in which an aqueous barium sulfate suspension with a relatively low concentration (about 40 to 50 W/V %) is injected into the intestine after washing of the intestine, discharged, and then air is insufflated before taking double contrast images, the Welin method (1953) in which an aqueous barium sulfate suspension (about 100 W/V %) is likewise charged into the intestine as a contrast medium after washing of the intestine as the preliminary treatment, and then discharged and again a small amount of the contrast medium is injected with insufflation of air before taking double contrast images and the Brown method (1963) in which the contents of the large intestine are removed without washing of the intestine by carrying out the preliminary treatment which applies strict dietary control and then administers laxative, and double contrast images are taken without accompaniment of discharging of the barium sulfate contrast medium. Further, the Brown method has been improved so as to be well adapted for Japanese. The thus improved method is now used as the modified Brown method for taking good double contrast images.

The modified Brown method is a method, in which after removal of the large intestine contents by application of a low fat and low residue meals (meals for contrast enema) and then administration of laxatives (saline laxatives and contact evacuant), 200 to 300 ml of an aqueous barium suspension of a relatively higher concentration of about 60 to 80 W/V % is injected into the intestine and, without being discharged, permitted to reach the whole large intestine so far as possible by rotating the patient (change of position) before insufflation of air for fluoroscopic photographing, and according to this method, it has become possible to visualize fine patterns of the large intestine mucosa as fine network patterns.

Generally speaking, when a known contrast medium is used, if the barium sulfate concentration is low, the amount of barium sulfate coated is not enough to give good double contrast image, while as the concentration is higher, the amount coated on the intestinal mucosa is increased, but the coating of barium sulfate on the intestinal mucosa surface becomes too thick to give a fine network pattern, and also difficulty is frequently encountered in moving the contrast medium throughout the intestinal tract. For this reason, ordinarily, a barium sulfate contrast medium with a concentration of 60 to 80 W/V % has been used.

The enema with double contrast method has been almost established according to the modified Brown method, but when propagation as the screening method for large intestine diseases is considered, there remain various problems such as demand of high degree of photographing technique, etc.

In the enema with double contrast method by use of a known contrast medium at a concentration of 60 W/V % or higher, due to X-ray intransmission at the portion where the contrast medium is pooled, no imaging of intestinal walls is possible, and further when another intestinal tract overlapping this in the transmitting direction exists, the overlapping intestinal portion cannot be visualized.

For this reason, for performing diagnosis without overlookings, it is ideal to carry out examination of the whole large intestine with as small amount of contrast medium as possible (around 150 to 200 ml) so that no pooling may occur. However, since the large intestine extends with a complicated steric structure, a considerable skill is technically required to deliver the injected contrast medium to the depth of the large intestine by way of rotating the patient.

Also, for coating the contrast medium well on intestinal walls, it is necessary to sufficiently perform rotation of the body of patient, which means that this method is an examination method requiring much burden on physically handicapped patients and aged people.

Further, since the contrast medium coated and then formed a solidified layer on intestinal walls is cracked with lapse of time, it is necessary to complete photographing relatively quickly, for which further technical skill is required.

DISCLOSURE OF THE INVENTION

The present inventors have made various studies with the aim at developing a contrast medium that is free, due to adequate X-ray transmissibility (radiolucency) and high coating ability, of the blind points in diagnosis as described above caused by contrast medium pooling portions and intestinal tracts overlapping them, and that requires no technical skill which has been a drawback of the enema with double contrast method of the prior art, and achieved the present invention whereby a contrast medium has now been provided that resolves the drawbacks of the prior art.

The present inventors have intensively studied first about the relationship between the concentration and the imaging ability of barium sulfate contrast medium, and consequently found that it has an adequate X-ray transmissibility at a barium sulfate concentration of 40 W/V % or less, and that the coating of the contrast medium to the large intestine mucosa is affected more greatly by the kind and the amount of additives rather than the barium sulfate concentration, particularly that gum tragacanth greatly affects the adhesive property and there exists the optimum amount to be added for the barium sulfate concentration.

More specifically, it has been found that, even with barium sulfate at lower concentrations, by using gum tragacanth as the additive and increasing its amount added as contrary to the barium sulfate concentration, the coating ability can be controlled so as to give a contrastability comparable with that attained with the barium sulfate concentration of the prior art.

Also, as a result of further studies, it has been also found that the contrast medium obtained by such knowledges as described above can be also used as extremely excellent contrast medium in computed tomography (X-ray CT).

The diagnostic imaging of large intestine diseases by computed tomography (X-ray CT) has been at present positioned as an auxiliary role for contrast enema or endoscopy examination. While examination by enema with double contrast method or endoscopy aims at imaging of fine lesions appearing on the large intestine mucosa surface, grasping of the progressing situation of lesions primarily on digestive tract walls or outside such walls is possible in computed tomography (X-ray CT), whereby informations with regard to cancer, such as information about the depth of wall invasion, invasion to adjacent organs, lymph node metastasis, peritoneal dissemination, remote metastasis (liver metastasis), etc. can be obtained, and therefore a high degree of diagnosis for large intestinal cancer becomes possible by combination of these examination methods.

However, when computed tomography (X-ray CT) is performed after the examination by way of enema with double contrast method of the prior art, since artifacts (artificial products) are produced by the contrast medium remaining within the intestinal tract, which interfere with diagnosis on image, no examination could be made before these were completely discharged.

For this reason, even when lesions may be found by contrast enema examination, computed tomography (X-ray CT) examination must be conducted on a later day, and since large intestine is a tubular organ which extends as if it travels round within the abdomen, and is yet slender with much flexing and twisting, identification of lesional sites could be made with difficulty in most cases.

At present, for identification of an intestinal tract by distinguishing it from other organs, there have been contrived various contrast methods such as the trans rectum Gastrografin infusion, the trans rectum olive oil infusion, the trans rectum air infusion, etc., but they were limited only to the lower part of the large intestine, and it has been desired to establish a medium contrast and a contrast method capable of obtaining higher degree of information in respect of the whole large intestine.

The contrast medium created by the present inventors, because barium sulfate at lower concentrations can be coated uniformly on intestinal tube through its excellent coating ability enables examination, even in computed tomography (X-ray CT), without formation of artifact (artificial product) which interferes with diagnosis.

Thus, the present invention has been accomplished on the basis of the findings as described above, and in accordance with the present invention, an excellent barium sulfate contrast medium for double contrast enema as well as for computed tomography (X-ray CT) is provided.

The present invention is described in more detail below.

The contrast medium of the present invention comprises an aqueous suspension containing barium sulfate at a low concentration of 15 to 35 W/V % and 2.0 to 0.5 W/V % of gum tragacanth. In this case, the concentration of gum tragacanth used is generally reduced in response to the increase in concentration of barium sulfate. By performing enema with double contrast method by use of 400 to 500 ml of the contrast medium of the present invention, the burden of the patient can be alleviated without requiring the high degree of technical skill in the prior art method, whereby simple, effective and excellent large intestine examination is rendered possible.

Further, when large intestine cancer is found, after enema with double contrast method, computed tomography (X-ray CT) can be immediately performed without formation of artifact (artificial product) which interferes with diagnosis, and yet examination can be made with the minimum degree of scanning intended to image the lesional site, thus enabling very efficient large intestine examination.

Also, since the contrast medium is coated on all the internal circumferences of the whole large intestine under the extended state, not only identification of large intestine and of surrounding lesional sites can be performed with ease, but also the relationship between intestinal tract walls and surrounding tissues can be clearly visualized for every large intestine site, whereby an extremely precise large intestine examination is rendered possible.

The contrast medium of the present invention may also contain various additives generally known in the art in addition to the above components, such as humectants, defoaming agents, preservatives, etc.

Also, in addition to gum tragacanth, for improvement of dispersibility or coating formability, for example, one or more kinds of suspending agents such as sodium carboxymethyl cellulose, sodium alginate, sodium chondroitin sulfate, gum arabic, methyl cellulose, gelatin, etc. can be used in combination.

The present invention is described in detail by referring to the following Examples.

EXAMPLE 1

In 95.6 liters of purified water were dissolved 0.05 kg of benzoic acid and 0.05 kg of dehydroacetic acid, and then 1.4 kg of tragacanth powder and 0.2 kg of sodium carboxymethyl cellulose were dissolved in the solution and then 20 kg of barium sulfate was added, followed by mixing and dispersing by means of a homomixer, etc. (about 20 W/V % concentration).

The suspension was sterilized by heating, cooled and then 0.01 kg of silicone resin as a defoaming agent was aseptically added and after the resulting mixture was thoroughly mixed, it was filled into a contrast medium injecting vessel in an amount of 400 ml (see, for example, Japanese Utility Model Publication No. 7245/1988).

Specific gravity: 1.175
Flow curve is shown in FIG. 1
Viscosity curve is shown in FIG. 2 E-type viscometer (Tokyo Keiki) Model EMD (cone plate 1.34"), measurement temperature 25° C.

EXAMPLE 2

In 94.4 liters of purified water were dissolved 0.05 kg of benzoic acid and 0.05 kg of dehydroacetic acid, and then 1.2 kg of tragacanth powder and 1.0 kg of gum arabic were dissolved in the solution and then 25 kg of barium sulfate was added, followed by mixing and dispersing by means of a homomixer, etc. (about 25 W/V % concentration).

The suspension was sterilized by heating, cooled and then 0.01 kg of silicone resin as a defoaming agent was aseptically added and after the resulting mixture was thoroughly mixed, it was filled into a contrast medium injecting vessel in an amount of 400 ml (see, for example, Japanese Utility Model Publication No. 7245/1988).

Specific gravity: 1.217
Flow curve is shown in FIG. 3
Viscosity curve is shown in FIG. 4 E-type viscometer (Tokyo Keiki) Model EMD (cone plate 1.34"), measurement temperature 25° C.

EXAMPLE 3

In 93.3 liters of purified water were dissolved 0.05 kg of benzoic acid and 0.05 kg of dehydroacetic acid, and then 1.0 kg of tragacanth powder and 0.25 kg of methyl cellulose were dissolved in the solution and then 30 kg of barium sulfate was added, followed by mixing and dispersing by means of a homomixer, etc. (about 30 W/V % concentration).

The suspension was sterilized by heating, cooled and then 0.01 kg of silicone resin as a defoaming agent was aseptically added and after the resulting mixture was thoroughly mixed, it was filled into a contrast medium injecting vessel in an amount of 400 ml (see, for example, Japanese Utility Model Publication No. 7245/1988).

Specific gravity: 1.250
Flow curve is shown in FIG. 5
Viscosity curve is shown in FIG. 6 E-type viscometer (Tokyo Keiki) Model EMD (cone plate 1.34"), measurement temperature 25° C.

The clinical evaluations obtained by use of the respective contrast media obtained in Examples 1 to 3 are as shown below. As the preliminary treatment, low residue food (enema food Colonoclean) and cathartics (Magcolol 125 ml and Laxoberon solution 10 ml) were used. The imaging ability was evaluated with 5 ranks as follows:

| Criteria for imaging ability evaluation | |
|---|---|
| +++: | readable and sharp image obtained |
| ++: | not sharp but readable image obtained |
| +: | image partially unreadable, but sufficient for diagnosis obtained |
| ±: | diagnostic value questionable |
| −: | no diagnostic value; hardly usable in examination |

| Evaluation contents | Contrast medium | | |
|---|---|---|---|
| | Example 1 | Example 2 | Example 3 |
| Imaging ability | | | |
| Rectum | +++ | +++ | +++ |
| Sigmoid colon | +++ | +++ | +++ |
| Descending colon | +++ | +++ | +++ |
| Transverse colon | +++ | +++ | +++ |
| Ascending colon | +++ | +++ | +++ |
| Ileocecum | +++ | +++ | +++ |
| Rotating the patient (coating, movement) | Possible at minimum limit | Possible at minimum limit | Possible at minimum limit |
| Burden on patient (rotating of body, examination time) | Little burden | Little burden | Little burden |
| Amount of contrast medium | Slightly deficient at 400 ml | Suitable at 400 ml | Suitable at 400 ml |
| Flowability | Although high in viscosity, movement of contrast medium was easy due to low barium sulfate concentrations. | | |
| X-ray transmissibility | Very good | Good | Good |
| Air bubble | Not recognized | Not recognized | Not recognized |
| Counterflow into the small intestine | None | None | None |
| Computed tomography (X-ray CT) | Examination immediately after enema with double contrast method is possible. Clear X-ray CT image without artifact obtained. | | |

In enema with double contrast method, all the contrast media obtained in Examples 1 to 3 exhibited a good coating ability in the rectum, sigmoid colon, descending colon, transverse colon, ascending colon and ileocecum, and clear Xray double contrast images of the whole large intestine could be obtained with the minimum degree of rotating body of the patient.

Although an amount of 400 ml of each contrast medium of the respective Examples was used, because most are coated onto the intestine wall, there were few pools to give a double contrast image of wide range, and even if a pool may be formed, it did not interfere with diagnosis due to optimum transmissibility.

When computed tomography (X-ray CT) was conducted subsequently after the enema with double contrast method, a clear X-ray CT image without artifact could be obtained, whereby identification of large intestine and identification of surrounding lesions could be easily done, and the relationship between the intestinal tract walls and surrounding tissues could be clearly visualized for every large intestine site.

EFFECT OF THE INVENTION

After preliminary treatment with meals for contrast enema and laxatives by performing enema with double contrast method by use of 400 to 500 ml of the contrast medium according to the present invention and computed tomography (X-ray CT), special effects as shown below can be obtained as compared with the prior art.

Examination by enema with double contrast method (1) Even in the overlapping or barium sulfate pooling portion of intestinal tubes, transmissibility optimal for observation of mucosal and image of margin can be obtained, whereby any lesions will never be overlooked.

(2) Coating with contrast medium can be effected simultaneously with its passage through intestinal tract, and no excessive postural change is required.

(3) By use of an amount of 400 to 500 ml, movement of ' contrast medium to the depth of large intestine is rendered easier and no postural change requiring technical skill is required.

(4) Due to little postural change, effective large intestine examination can be done for physically handicapped patients or aged people.

(5) Even by use of an amount of 400 to 500 ml, there are few pools, whereby double contrast photographs can be obtained over a wide range.

(6) X-ray absorption difference within the range of imaging becomes smaller, whereby contrast can be easily controlled under X-ray photographing conditions to give a photograph with more information.

(7) Due to no excessive counterflow of contrast medium into the lower part of the small intestine, overlapping with the lower part of the large intestine can be prevented.

(8) The pretreatment time for examination is remarkably short.

(9) Due to good water retentivity, the layer of contrast medium coated will not crack for a long time. Accordingly, the examination time can be prolonged.

(10) Since the absolute amount of barium sulfate injected into intestine is small, discharging after examiantion can be performed with ease.

Computed tomography (X-ray CT)

(1) Computed tomography (X-ray CT) is possible without formation of artifact (artificial product) which interferes with diagnosis, and examination of the afflicted portion can be made immediately subsequent to enema with double contrast method.

(2) Since computed tomography (X-ray CT) can be performed immediately after enema with double contrast method, the contrast medium is coated onto all the internal circumferences of the whole large intestine under the extended state, whereby identification of the large intestine and surrounding lesions can be easily made and the relationship between the intestinal tract walls and surrounding tissues can be clearly visualized for every large intestine site.

(3) Since lesions pointed out by contrast enema examination can be immediately observed by computed tomography (X-ray CT), it becomes possible to perform examination with the minimum degree of scanning by relying on the lesional site identified by the slit scanography (scout view) as the target, whereby the dose of exposure of the patient can be reduced.

(4) Since examination by enema with double contrast method and computed tomography (X-ray CT) can be performed continuously, the advantages, such as omission of one of the pretreatments and shortening of the time itself, can be achieved, whereby examination time and labor are remarkably reduced.

Figure 1:
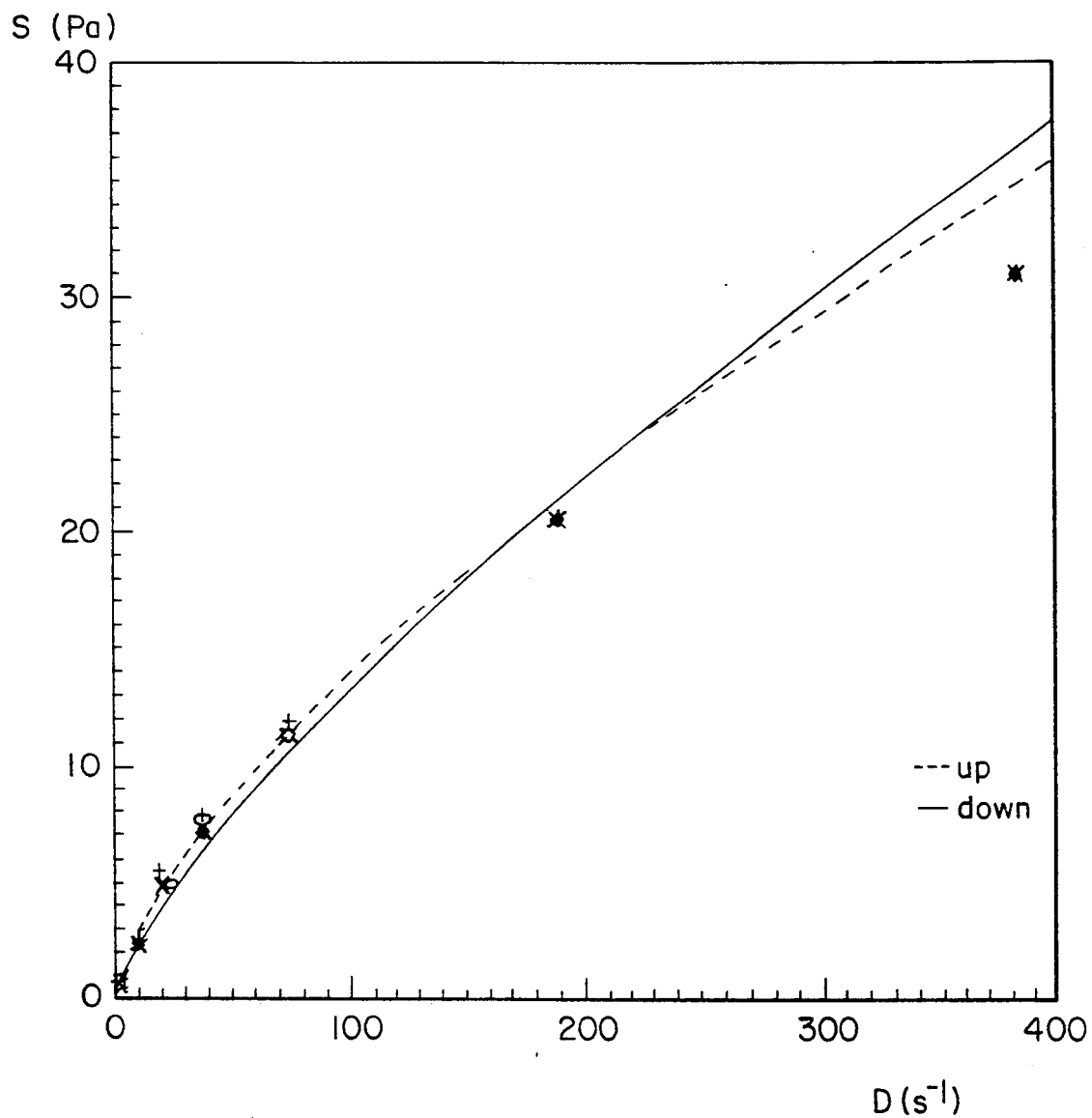
FIG. 1 is a graph showing the flow curve of the contrast medium of the present invention obtained in Example 1.
Figure 2:
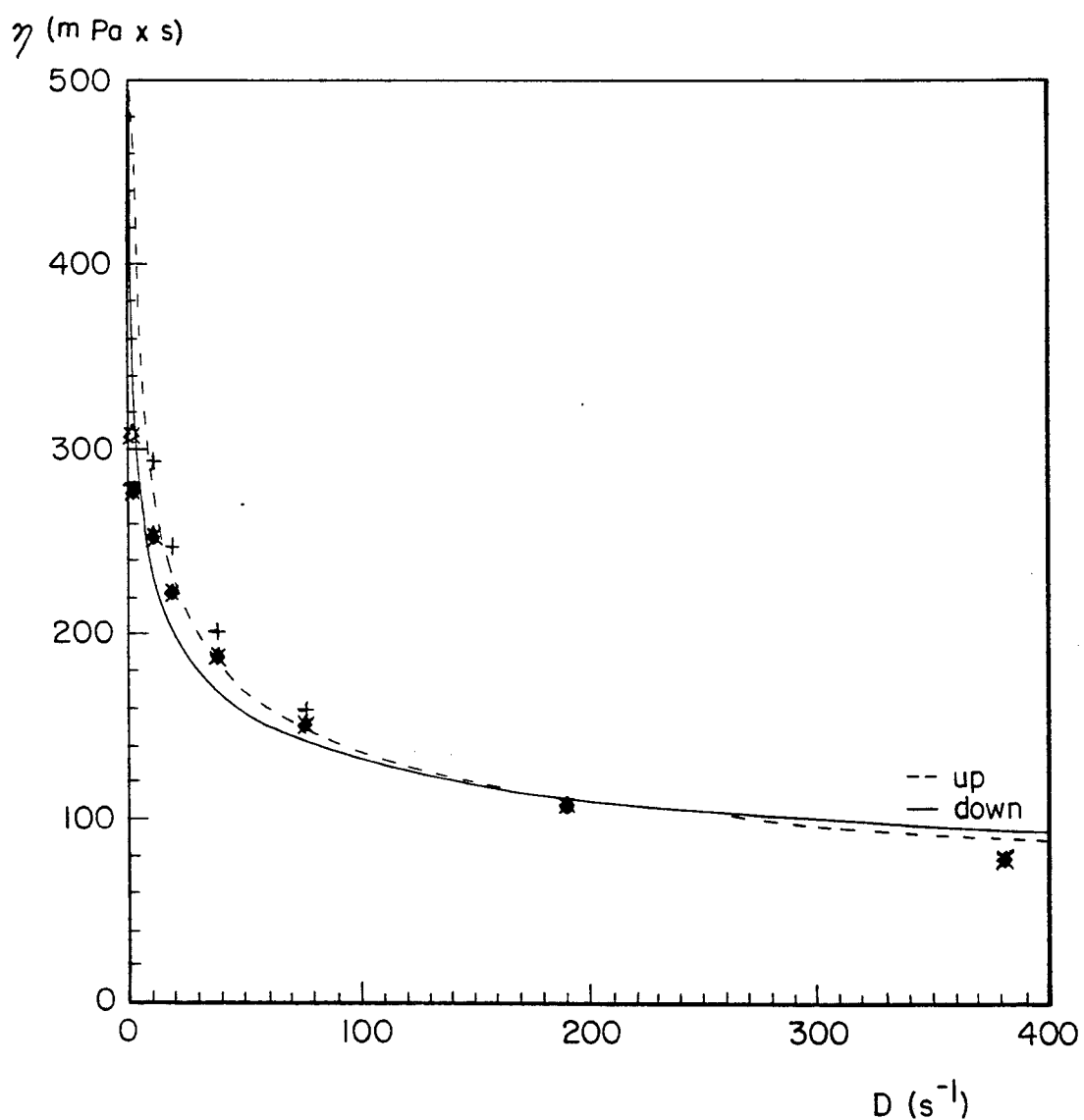
FIG. 2 is a graph showing the viscosity curve of the same contrast medium (Example 1)
Figure 3:
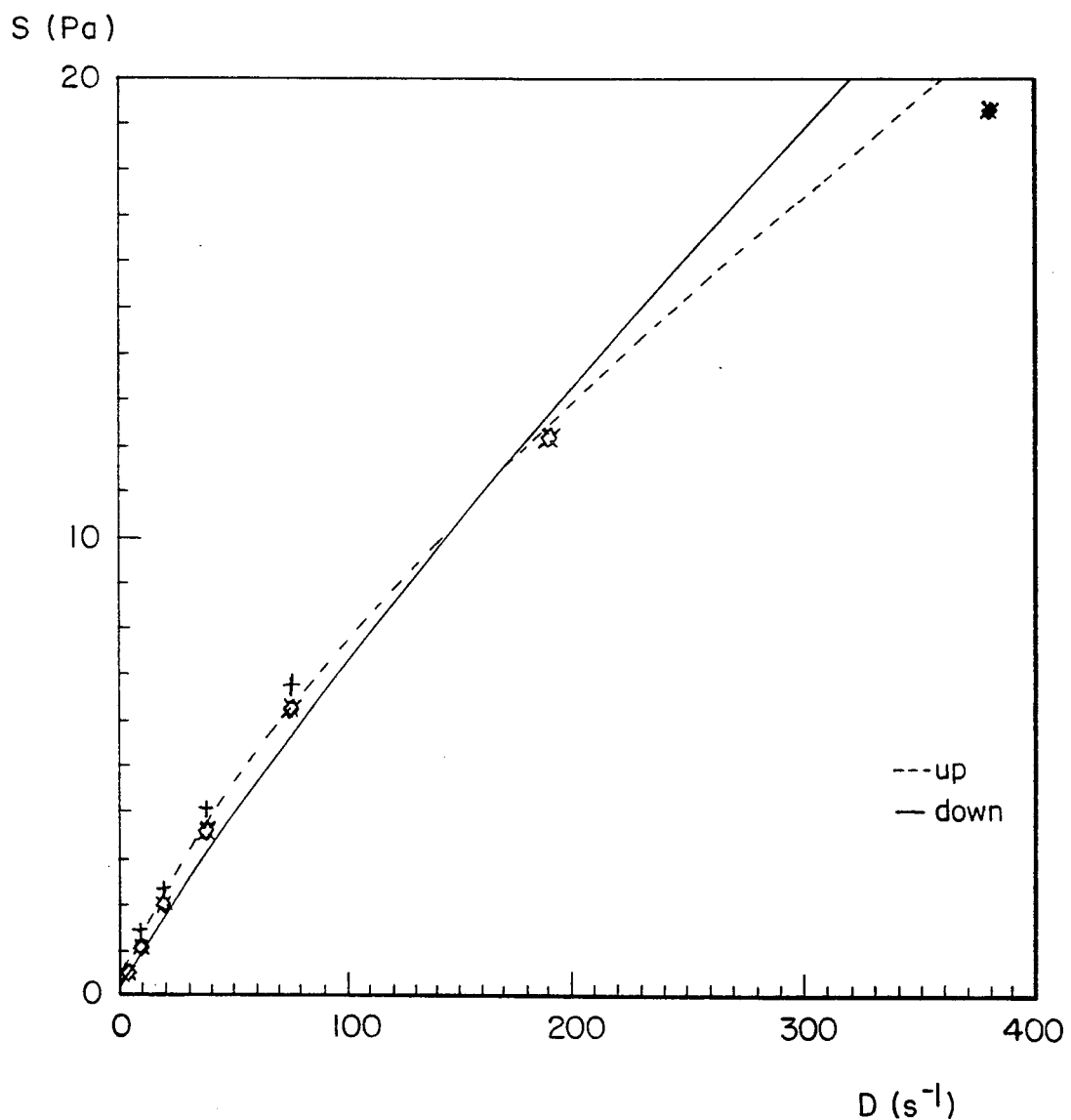
FIG. 3 is a graph showing the flow curve of the contrast medium of the present invention obtained in Example 2.
Figure 4:
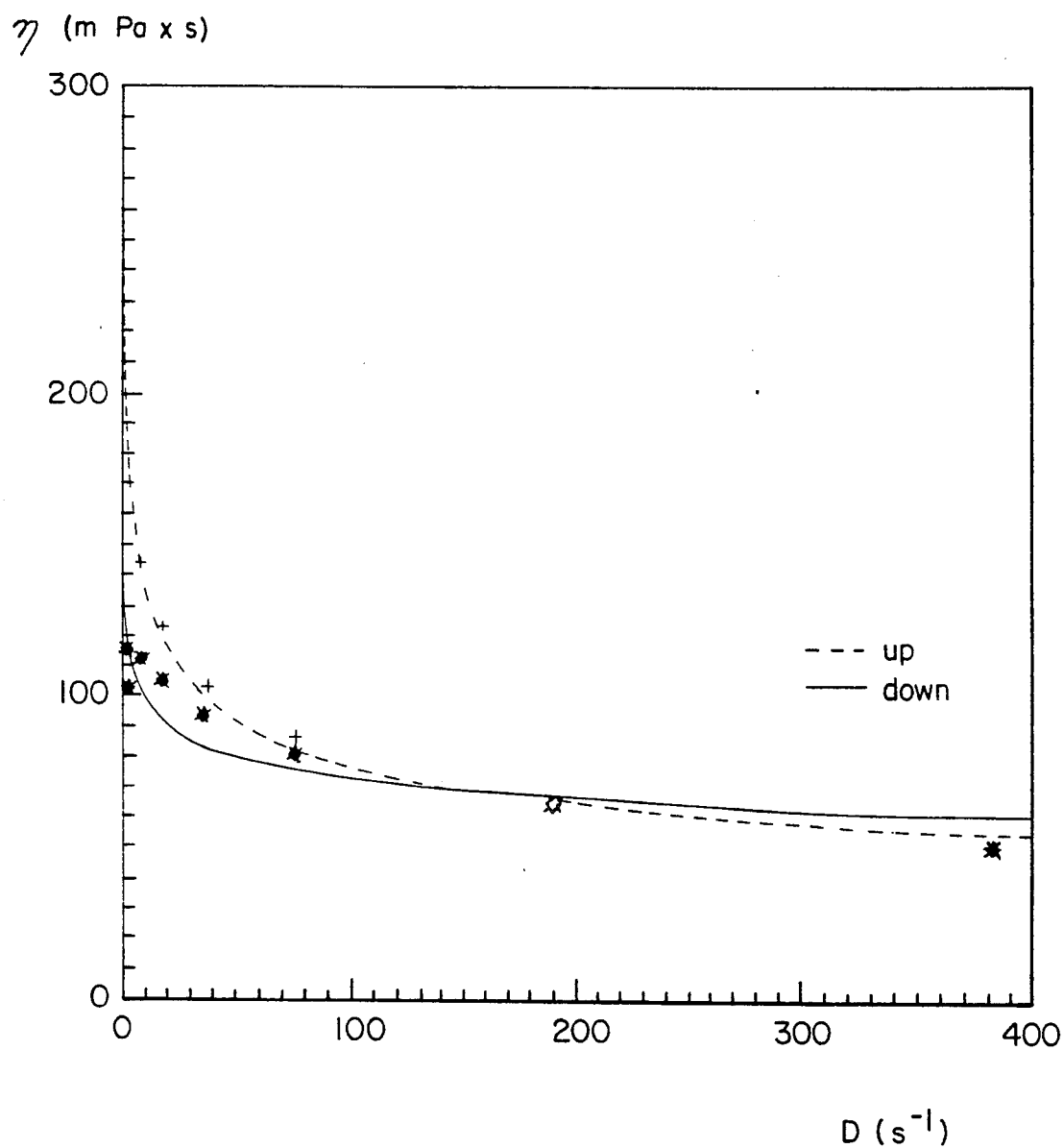
FIG. 4 is a graph showing the viscosity curve of the same contrast medium (Example 2)
Figure 5:
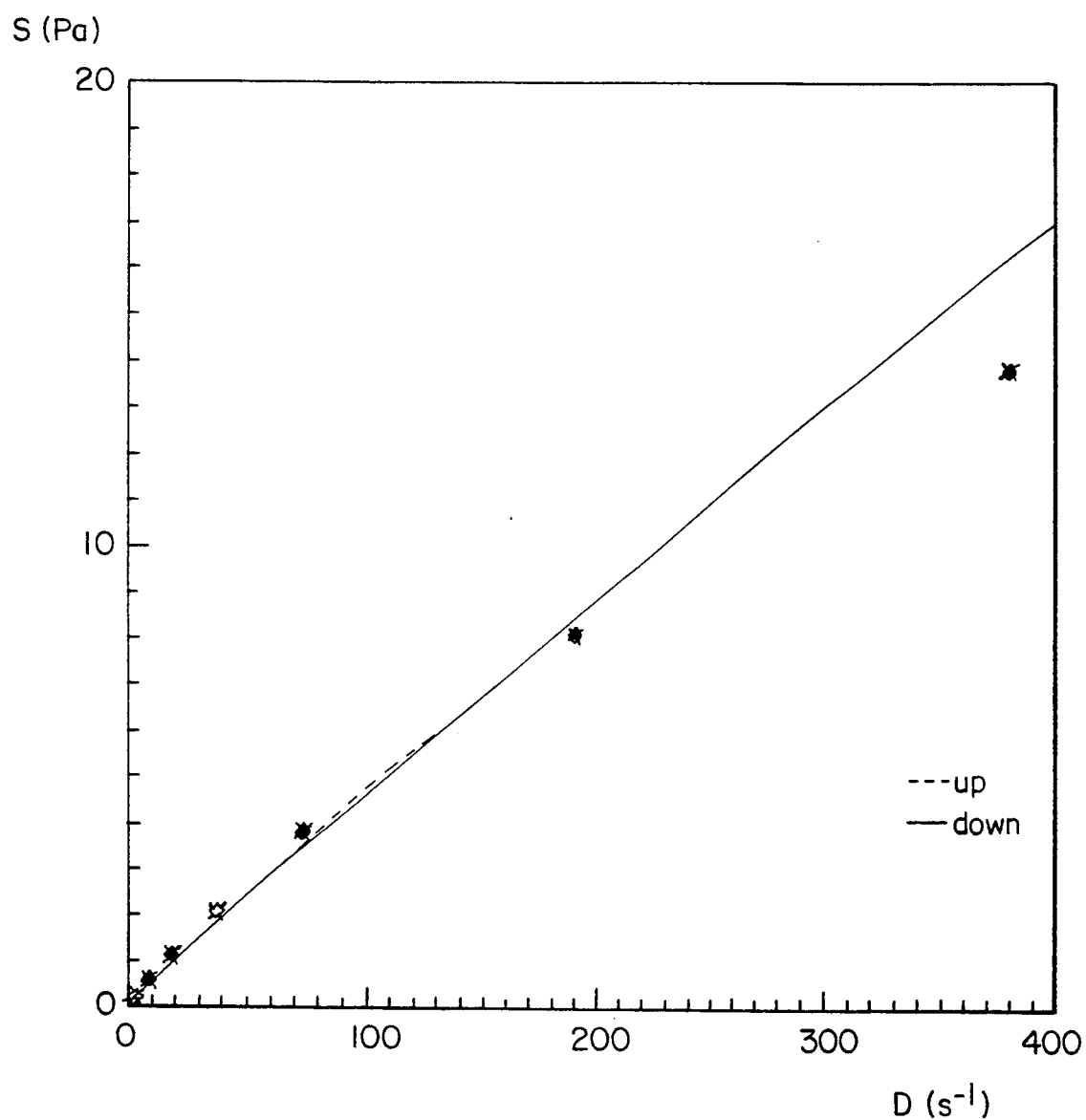
FIG. 5 is a graph showing the flow curve of the contrast medium of the present invention obtained in Example 3.
Figure 6:
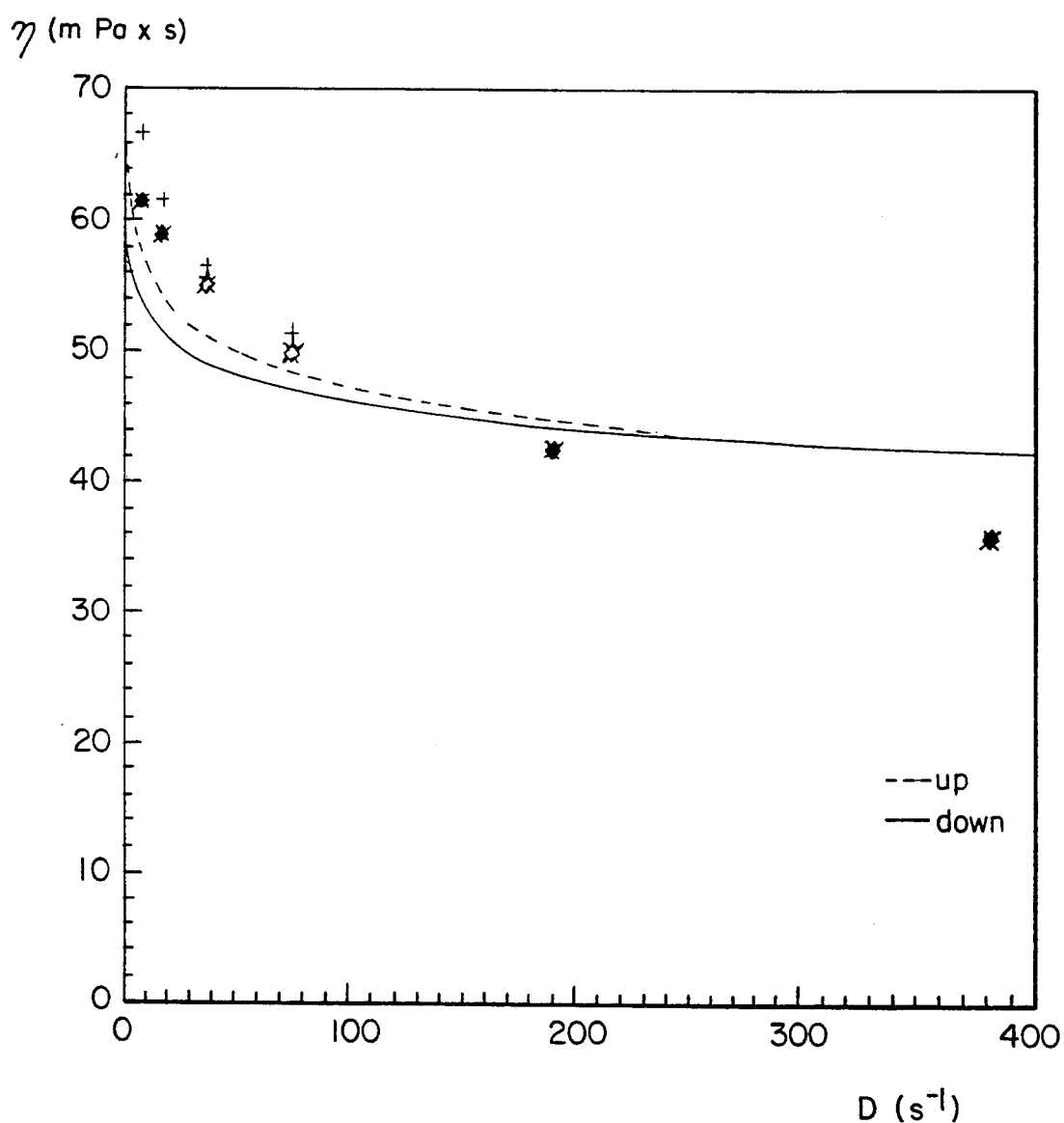
FIG. 6 is a graph showing the viscosity curve of the same contrast medium (Example 3).

What is claimed is:

1. A contrast medium for use for X-ray examination of the large intestine according to the double contrast method, in the form of an enema which comprises an aqueous suspension containing 20 to 30 W/V % of barium sulfate, 2.0 to 0.5 W/V % of gum tragacanth, and one or more suspending agents selected from the group consisting of sodium carboxymethyl cellulose and gum arabic.

* * * * *